US012004568B2

(12) United States Patent
O'Hare et al.

(10) Patent No.: US 12,004,568 B2
(45) Date of Patent: Jun. 11, 2024

(54) TEMPERATURE REGULATION FOR PERSONAL VAPORIZING DEVICE (71) Applicant: JT International S.A., Geneva (CH)

(72) Inventors: Aidan O'Hare, Coventry (GB); Brian Molyneux, Poole (GB)

(73) Assignee: JT International S.A. (CH)

( * ) Notice: Subject to any disclaimer, the term of this patent is extended or adjusted under 35 U.S.C. 154(b) by 771 days.

(21) Appl. No.: 17/256,751

(22) PCT Filed: Jul. 19, 2019

(86) PCT No.: PCT/EP2019/069560
§ 371 (c)(1),
(2) Date: Dec. 29, 2020

(87) PCT Pub. No.: WO2020/020788
PCT Pub. Date: Jan. 30, 2020

(65) Prior Publication Data
US 2021/0259314 A1 Aug. 26, 2021

(30) Foreign Application Priority Data

Jul. 24, 2018 (EP) .................................... 18185092

(51) Int. Cl.
*A24F 40/48* (2020.01)
*A24F 40/10* (2020.01)
*A24F 40/46* (2020.01)
*A24F 40/57* (2020.01)

(52) U.S. Cl.
CPC ............. *A24F 40/48* (2020.01); *A24F 40/10* (2020.01); *A24F 40/46* (2020.01); *A24F 40/57* (2020.01)

(58) Field of Classification Search
None
See application file for complete search history.

(56) References Cited

U.S. PATENT DOCUMENTS

| 9,597,466 B2 * | 3/2017 | Henry, Jr. ............ A61M 11/042 |
| 2011/0265806 A1 | 11/2011 | Alarcon et al. |
| 2014/0014126 A1 | 1/2014 | Peleg et al. |
| 2014/0096781 A1 | 4/2014 | Sears et al. |
| 2015/0192084 A1 | 7/2015 | Surnilla et al. |

(Continued)

FOREIGN PATENT DOCUMENTS

| CN | 106072766 A | 11/2016 |
| WO | 2010052697 A1 | 5/2010 |

(Continued)

OTHER PUBLICATIONS

International Search Report for Application No. PCT/EP2019/069560, dated Dec. 13, 2019, pp. 1-8.

*Primary Examiner* — Ross N Gushi
(74) *Attorney, Agent, or Firm* — Lerner David LLP (57) ABSTRACT A cartridge for a personal vaporizing device includes a liquid store, a liquid transfer element, a heating element, a first power terminal and a second power terminal connected to the heating element, and a memory configured to store a first reference value indicating the resistance of the heating element at a reference temperature or reference. A method of manufacturing such a cartridge is also provided. A main body of a personal vaporizing device has a cartridge seating configured to receive such a cartridge.

18 Claims, 6 Drawing Sheets

(56) References Cited

U.S. PATENT DOCUMENTS

| | | |
|---|---|---|
| 2017/0006917 A1 | 1/2017 | Alvarez |
| 2017/0043996 A1 | 2/2017 | Murison et al. |
| 2017/0245553 A1 | 8/2017 | Reevell |
| 2017/0347717 A1 | 12/2017 | Matsumoto et al. |
| 2018/0093054 A1* | 4/2018 | Bowen ................ A61M 11/042 |

FOREIGN PATENT DOCUMENTS

| | | |
|---|---|---|
| WO | 2013098396 A2 | 7/2013 |
| WO | 2013098398 A2 | 7/2013 |
| WO | 2015138560 A1 | 9/2015 |
| WO | 2015192084 A1 | 12/2015 |
| WO | 2016143079 A1 | 9/2016 |
| WO | 2017001819 A1 | 1/2017 |
| WO | 2017205692 A1 | 11/2017 |
| WO | 2017207195 A1 | 12/2017 |
| WO | 2018087740 A1 | 5/2018 |

* cited by examiner

TEMPERATURE REGULATION FOR PERSONAL VAPORIZING DEVICE

CROSS-REFERENCE TO RELATED APPLICATIONS

The present application is a national phase entry under 35 U.S.C. § 371 of International Application No. PCT/EP2019/069560, filed Jul. 19, 2019, published in English, which claims priority to European Application No. 18185092.6 filed Jul. 24, 2018, the disclosures of which are incorporated herein by reference.

FIELD OF THE INVENTION

The present invention relates to personal vaporizing devices, such as electronic cigarettes with an improved temperature regulation. In particular, the invention relates to a personal vaporizing device comprising an improved control of the power applied to a heating element in a removable/disposable consumable, and to such removable/disposable consumable for such a personal vaporizing device which allows the personal vaporizing device to control power more accurately.

BACKGROUND

Personal vaporizing devices such as electronic cigarettes are an alternative to conventional cigarettes. Instead of generating a combustion smoke, they vaporize a material such as a liquid, which can be inhaled by a user. A vaporizing liquid typically comprises an aerosol-forming substance, such as glycerin or propylene glycol that creates the vapor. Other common substances in the liquid are nicotine and various flavorings. US 2017/245553 A1 (REEVELL TONY [GB]), 31 Aug. 2017 (2017-08-31) relates to an electrically operated aerosol-generating system with temperature sensor. US 2017/006917 A1 (ALVAREZ DAVID [US]), 12 Jan. 2017 relates to an E-vapor device including capsule containing pre-vapor formulation. US 2015/192084 A1 (EVOLV LLC [US]), 17 Dec. 2015 relates to methods and systems for fuel ethanol content determination via oxygen sensor.

The electronic cigarette is a hand-held inhaler system or personal vaporizing system, comprising a mouthpiece portion, a store for vaporizing material (e.g. a liquid store), a vaporizer unit or heating element and a power supply unit. Vaporization occurs when the heating element heats up the vaporizing material for instance a vaporizing liquid in or on a liquid transfer element (such as a wick) to a temperature exceeding the boiling temperature of the material (e.g. liquid), where vaporization occurs.

The store for vaporizing material or liquid store can be configured as a refillable reservoir. Alternatively, the electronic cigarette may comprise a seating, e.g. in the mouthpiece section, which is configured to receive removable/disposable consumables in the form of cartridges. The cartridges comprising a liquid store and a vaporizer in a single unit are often referred to as "cartomizers".

The electronic cigarette operates the heating element at a temperature at which vaporization occurs. As mentioned above, the liquid is vaporized when the temperature of the liquid adjacent to the heating element exceeds the boiling temperature. It is advantageous to control and regulate the temperature of the heating element, for several reasons. In particular, regulation ensures that the vaporization is efficient. Furthermore, it avoids overheating the liquid and the liquid transfer element. If overheating occurs due to an excessive power applied to the heating element, or if the liquid store is depleted and the liquid transfer element becomes dry, undesired volatile compounds may form.

It is therefore an object of the present invention to provide an improved temperature regulation for an electronic cigarette.

SUMMARY

One aspect of the present invention is based on the principle that the temperature of the heating element can be measured by applying a current through the heating element, measuring the resulting voltage at its ends, and determining the resistance of the heating element therefrom. As the resistance increases with temperature, if the inherent resistance characteristics of the heating element, it is possible to estimate the temperature of the heating element from its current resistance, obtained through measuring the voltage.

The vaporization temperature can be accurately controlled if the measured resistance of the heating element and the information available about the inherent resistance characteristics of the heating element are accurate. The inherent resistance characteristics of the heating element can be estimated if its resistance at a certain temperature is known. However, the resistance of the heating element varies between different disposable consumables used with an electronic cigarette, already due to irregularities in the manufacturing process of the disposables. Thus, according to another aspect of the present invention, a reference value indicating the resistance of an electrical element in the consumable including the heating element at a reference temperature or reference temperature range of the heating element is stored on the consumable and provided to the main body of the electronic cigarette, so that the electronic cigarette can determine the inherent resistance characteristics of the currently used heating element more accurately.

The invention is defined in the independent claims directed to a consumable for a personal vaporizing device, methods of manufacturing a consumable for a personal vaporizing device, a main body of a personal vaporizing device, a personal vaporizing device, methods for determining the temperature of a heating element in a consumable of a personal vaporizing device, and a method for regulating the power applied to the heating element in a consumable of a personal vaporizing device. The details of preferred embodiments are set forth in the dependent claims, the accompanying drawings and the description below.

One aspect of the invention relates to a consumable for a personal vaporizing device, the consumable comprising: a liquid store, a liquid transfer element, a heating element, a first power terminal and a second power terminal connected to the heating element, and a memory configured to store a first reference value indicating the resistance of an electrical element in the consumable including the heating element at a reference temperature or reference temperature range of the heating element. Such a consumable is advantageously configured such that a resistance of an electrical element comprising the heating element can be precisely determined using a reference value, resistance from which the temperature of the heating element can be more precisely derived.

In an embodiment of the consumable, the electrical element is an open loop of an electronic circuit.

In an embodiment of the consumable, the electrical element is the heating element.

In an embodiment of the cartridge, the memory further comprises a predetermined temperature coefficient of resistivity a related to the material of the heating element.

In an embodiment of the consumable, the memory of the consumable is configured to store a second reference value indicating the resistance of an open loop of an electronic circuit including the heating element or the difference between the resistance of the heating element and an open loop of an electronic circuit including the heating element. Consequently, the second reference value can be used to determine even more precisely the resistance of the temperature of the heating element.

In an embodiment of the consumable, the endpoints of the open loop are the first and second power terminals.

In an embodiment the consumable, it is further configured to provide the first and/or second reference values to a main body of the personal vaporizing device, preferably, by means of one or more data terminals on the consumable.

In an embodiment of the consumable, it is not configured to have its liquid store refurbished.

In an embodiment of the consumable, it comprises a mouthpiece portion.

In an embodiment of the consumable, the heating element is a heating coil.

In an embodiment of the consumable, the memory is further configured to store usage data on the usage of the consumable, authentication data on the consumable, type, composition, flavor or remaining quantity of a liquid L contained in the consumable, and/or best-before date of the consumable.

In an embodiment of the consumable, it is further configured to provide the data stored in the memory to a main body of the personal vaporizing device, preferably by means of one or more data terminals on the consumable.

In an embodiment, the consumable can be a cartridge comprising a liquid store, a heater and a liquid transfer element.

In another embodiment, the consumable can be an atomizer comprising a heater and a liquid transfer element. The atomizer can advantageously be used together with a stationary and refillable liquid store (often referred to as an "open-tank"). The electrical connectors of the main body can therefore be located in the proximity of an atomizer seating. As a result, the atomizer can be contacted in a similar way by a first pair of electrical connectors configured to provide battery power to the atomizer and a second pair of electrical connectors configured to establish a measurement circuit.

Another aspect of the invention relates to a method of manufacturing the consumable according to preceding embodiments, wherein the first reference value is obtained by measuring the resistance of the electrical element and measuring the ambient temperature, preferably before its assembly into the cartridge. In an embodiment the ambient temperature and the temperature of the heating element substantially corresponds to the reference temperature or lies within the reference temperature range.

In another embodiment, the ambient temperature corresponds to the temperature of the heating element, which differ from the reference temperature and wherein the resistance reference value at the reference temperature is calculated by adjusting the measured resistance value by using the formula $R=R_{ref}[1+\alpha(T-T_{ref})]$, where R is the current resistance of the coil at the current ambient temperature T, $R_{ref}$ is the reference resistance of the coil at reference temperature $T_{ref}$, $\alpha$ is the temperature coefficient of resistance of the coil material and T is the current temperature in ° C. of the heating element Another aspect of the invention relates to a method of manufacturing the consumable according to preceding embodiments, wherein the first reference value or the second reference value, respectively, is obtained by measuring the resistance of the open loop after the assembly of the open loop while the temperature of the heating element substantially corresponds to the reference temperature or lies within the reference temperature range.

Another aspect of the invention relates to a main body of a personal vaporizing device, the main body having a consumable seating configured to receive a consumable comprising: a liquid store, a liquid transfer element, a heating element, and a first power terminal and a second power terminal connected to the heating element; wherein the consumable seating comprises: a first pair of electrical connectors configured to establish an electrical circuit when connected to a first power terminal and a second power terminal of the consumable such that power is supplied to the consumable, and a second pair of electrical connectors configured to establish a measuring circuit for measuring the voltage between the first and the second power terminals of the consumable. Such a main body is configured to be capable of measuring more precisely a resistance of the heating element of a consumable, and consequently is capable of providing an improved regulation of its temperature.

In an embodiment of the main body, it further comprises a controller configured to determine the resistance of the electrical circuit comprising the heating element between the first and second power terminals by means of the voltage measured by the measuring circuit.

In an embodiment of the main body, it is further configured to obtain a reference value indicating the resistance of an electrical element in the consumable including the heating element at a reference temperature or reference temperature range of the heating element; and to determine the temperature of the heating element by means of comparing the determined resistance with the resistance indicated by the reference value.

In an embodiment, the controller is configured to determine a current temperature by executing a functional relationship of $R=R_{ref}[1+\alpha(T-T_{ref})]$ when interrogated by the controller, where R is the current resistance of the coil at the current temperature T, $R_{ref}$ is the reference resistance of the coil at reference temperature $T_{ref}$, $\alpha$ is the temperature coefficient of resistance of the coil material and T is the coil current temperature in ° C.

In an embodiment of the main body, the controller is further configured to: obtain a first reference value indicating the resistance of the heating element at a reference temperature or reference temperature range of the heating element; obtain a second reference value indicating the resistance of an open loop of an electronic circuit including the heating element or the difference between the resistance of the heating element and an open loop of an electronic circuit including the heating element; determine the resistance of the electrical circuit comprising the heating element between the first and the second power terminals by means of the measured voltage; determine the resistance of the heating element by means of the determined resistance of the electrical circuit and the second reference value; determine the temperature of the heating element by means of comparing the determined resistance of the heating element with the resistance indicated by the first reference value.

In an embodiment of the main body, the controller obtains the reference value or the first and/or second reference value, respectively, from the consumable.

In an embodiment of the main body, it further comprises data connectors for obtaining the reference values from the consumable.

In an embodiment of the main body, it is configured to regulate the power applied to the heating element in the consumable depending on the determined temperature of the heating element.

Another aspect of the invention relates to a personal vaporizing device comprising a consumable according to one of the preceding embodiments, and a main body according to one of the preceding embodiments.

Another aspect of the invention relates to a method for determining the temperature of a heating element in a consumable of a personal vaporizing device, comprising the steps of: measuring a voltage over a first and second power terminal connected with the heating element; determining a resistance of an electrical element in the consumable including the heating element between the first and second power terminals by means of the measured voltage; obtaining a first reference value indicating the resistance of an electrical element in the consumable including the heating element at a reference temperature or reference temperature range of the heating element; and determining the temperature of the heating element by means of comparing the determined resistance with the resistance indicated by the first reference value.

Another aspect of the invention relates to a method for determining the temperature of a heating element in a consumable of a personal vaporizing device, comprising the steps of: measuring a voltage over a first and second power terminal connected with the heating element; obtaining a first reference value indicating the resistance of the heating element at a reference temperature or reference temperature range of the heating element; obtaining a second reference value indicating the resistance of an open loop of an electronic circuit including the heating element or the difference between the resistance of the heating element and an open loop of an electronic circuit including the heating element; determining the resistance of the electrical circuit comprising the heating element between the first and the second power terminals by means of the measured voltage; determining the resistance of the heating element by means of the determined resistance of the electrical circuit and the second reference value; determining the temperature of the heating element by means of comparing the determined resistance of the heating element with the resistance indicated by the first reference value.

Another aspect of the invention is related to a method of regulating the power applied to a heating element in a consumable of a personal vaporizing device, the method comprising executing a feedback loop comprising: determining the temperature of the heating element in accordance with the method of one of the preceding embodiments, and regulating the power supplied to the heating element depending on the determined temperature.

The invention is also directed to a consumable for a personal vaporizing device, and a personal vaporizing device comprising a main body and a consumable.

One aspect of the invention relates to a cartridge for releasable connection to an electronic cigarette, the cartridge comprises a substance to be vaporized and is provided with an electrical circuitry, wherein the electrical circuitry comprises: circuit terminals configured to engage with circuit connectors located on a main body of the electronic cigarette and configured to establish a data connection between the cartridge and the main body, a memory for storing data, and wherein the circuit terminals of the cartridge are located on a housing of the cartridge.

In one embodiment of the first aspect of the invention, the cartridge further comprises a controller configured to read and write data on the memory.

In one embodiment of the first aspect of the invention, the circuit terminals are grouped together on a rigid support, preferably a printed circuit board (PCB).

In one embodiment of the first aspect of the invention, the controller and the memory are located on the rigid support, preferably a printed circuit board (PCB).

In one embodiment of the first aspect of the invention, the cartridge comprises a connection portion which is configured to connect to the main body of the electronic cigarette, wherein the connection portion is provided with a lateral surface with a direction coinciding with a longitudinal direction of the cartridge, substantially parallel to an insertion direction of the cartridge into the main body, and wherein the circuit terminals are located in said connection portion on said lateral surface.

In one embodiment of the first aspect of the invention, the cartridge has a first and a second pair of lateral surfaces substantially parallel to each other, the widths of the sides of the second pair being wider than the widths of the sides of the first pair, and wherein the connection portion is located on the first surface.

In one embodiment of the first aspect of the invention, all circuit terminals are arranged on the same plane.

In one embodiment of the first aspect of the invention, the distance between two neighboring circuit terminals is comprised between 20 mm and 0.05 mm, preferably 10 mm and 0.1 mm, more preferably 5 mm and 0.15 mm, even more preferably 2 mm and 0.2 mm, and most preferably 1 mm and 0.2 mm.

In one embodiment of the first aspect of the invention, the one or more circuit terminals, or at least initial connection portions thereof, are provided at different positions in the longitudinal direction of the cartridge relative to the longitudinal positions of the circuit connectors, or at least initial connection portions thereof, whereby the circuit terminals are connectable to the circuit connectors at different times in a predetermined sequence upon connection of the cartridge to the main body of the electronic cigarette.

In one embodiment of the first aspect of the invention, the cartridge further comprises power terminals which are configured to provide power from the main body to heat a heating element comprised by the cartridge.

In one embodiment of the first aspect of the invention, the power terminals are elongated and arranged in the connection portion with their longitudinal direction substantially parallel to the insertion direction in which the cartridge is connected to the main body.

In one embodiment of the first aspect of the invention, all power terminals are arranged on the same plane.

In one embodiment of the first aspect of the invention, the power terminals are located on the plane of the circuit terminals.

In one embodiment of the first aspect of the invention, the distance between two neighboring power terminals is comprised between 30 mm and 0.05 mm, preferably 10 mm and 0.1 mm, more preferably 5 mm and 0.15 mm, even more preferably 2 mm and 0.2 mm, even most preferably 1 mm and 0.2 mm.

In one embodiment of the first aspect of the invention, the PCB of the cartridge has a cut-out for accommodating the power terminals.

A second aspect of the present invention is an electronic cigarette comprising a main body and a cartridge in accordance with the first aspect of the invention, wherein the main body comprises circuit connectors located in a cartridge seating at a distal end of the main body and configured for connection with corresponding circuit terminals of the cartridge, and the circuit terminals of the cartridge are located on a lateral side of the cartridge and the connectors of the main body are located on a lateral side of a capsule seating, whereby the circuit connectors and the circuit terminals are configured to engage with each other in a direction coinciding with a longitudinal direction of the main body.

In one embodiment of the second aspect of the invention, the circuit terminals of the cartridge and the connectors of the main body are configured such that one or more of the circuit terminals are connected to the corresponding circuit connectors at different times when the cartridge is connected to the main body.

In one embodiment of the second aspect of the invention, the circuit connectors are elongated and arranged with their longitudinal direction substantially parallel to the inserting direction in which the cartridge is connected to the main body.

In one embodiment of the second aspect of the invention, the cartridge further comprises power terminals which are configured to provide power from the main body to heat a heating element comprised by the cartridge, and wherein the main body comprises power connectors for connection with corresponding ones of the power terminals of the cartridge, and the electronic cigarette is configured such that the power terminals are connected to the power connectors before the circuit terminals are connected to the circuit connectors when the cartridge is connected to the main body.

In one embodiment of the second aspect of the invention, the circuit connectors have different lengths.

In one embodiment of the second aspect of the invention, the circuit terminals comprise a negative circuit terminal and wherein the negative circuit terminal is connected before the other circuit terminals when the cartridge is connected to the main body.

In one embodiment of the second aspect of the invention, the connectors or/and the terminals of the electronic cigarette are resilient such that when the main body and the cartridge are connected, the connectors are biased in order to create a biasing force which maintains the contact between the connectors and their respective terminals.

In one embodiment of the second aspect of the invention, the connectors on the main body have free ends and wherein these free ends are held in a connector guard (60).

In one embodiment of the second aspect of the invention, the connector guard, is also configured to protect the sides of the arrangements of connectors.

In one embodiment of the second aspect of the invention, the connection between the housing of the cartridge and the cartridge seating is a magnetic connection.

In one embodiment of the second aspect of the invention, the cartridge is provided with a magnetic connection means for connecting the cartridge to the cartridge seating, wherein one of the cartridge seating or the cartridge is provided with a ferromagnetic member and the other is provided with a magnet.

BRIEF DESCRIPTION OF THE DRAWINGS

FIG. 1b is a schematic cross-sectional view of the electronic cigarette of FIG. 1a.

DETAILED DESCRIPTION OF PREFERRED EMBODIMENTS

In the following, preferred embodiments of the present invention will be described in detail with reference to the accompanying drawings. In the description of the drawings, the same or similar reference numerals denote the same or similar parts. It should be noted that the drawings are schematic, and the ratios of dimensions and the like may be different from the actual ones.

Figure 1A:
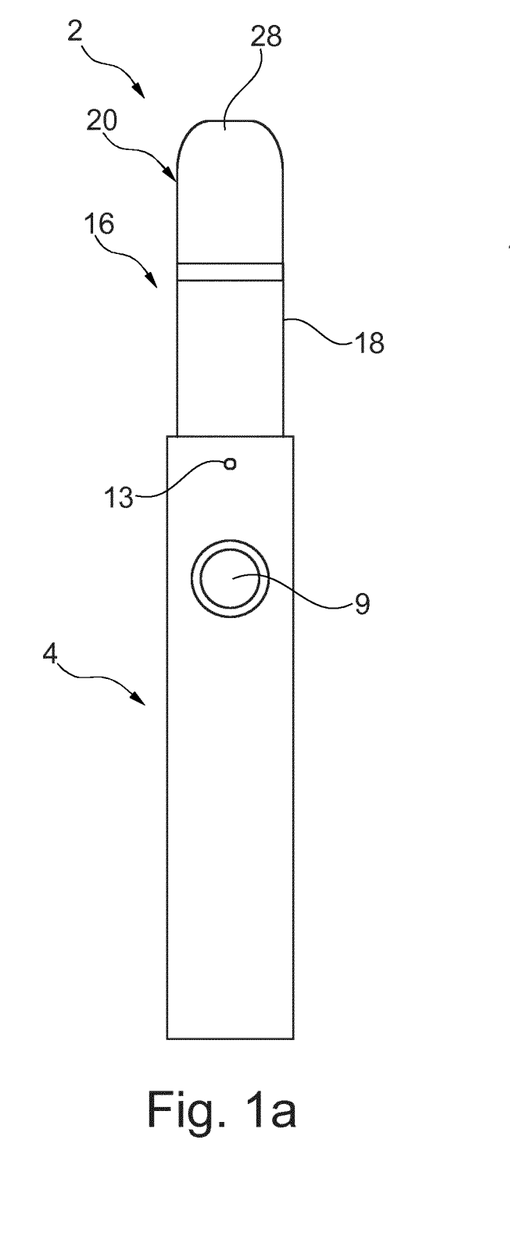
FIG. 1a is a schematic perspective view of an electronic cigarette according to an exemplary embodiment of the present invention.
Figure 1B:
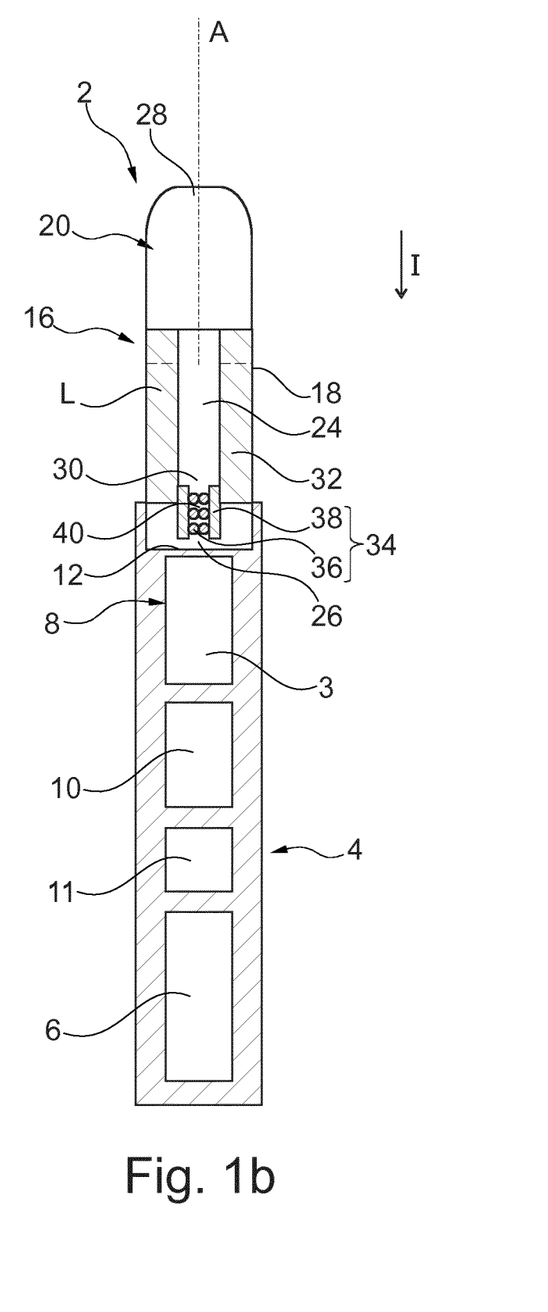
Figure 2:
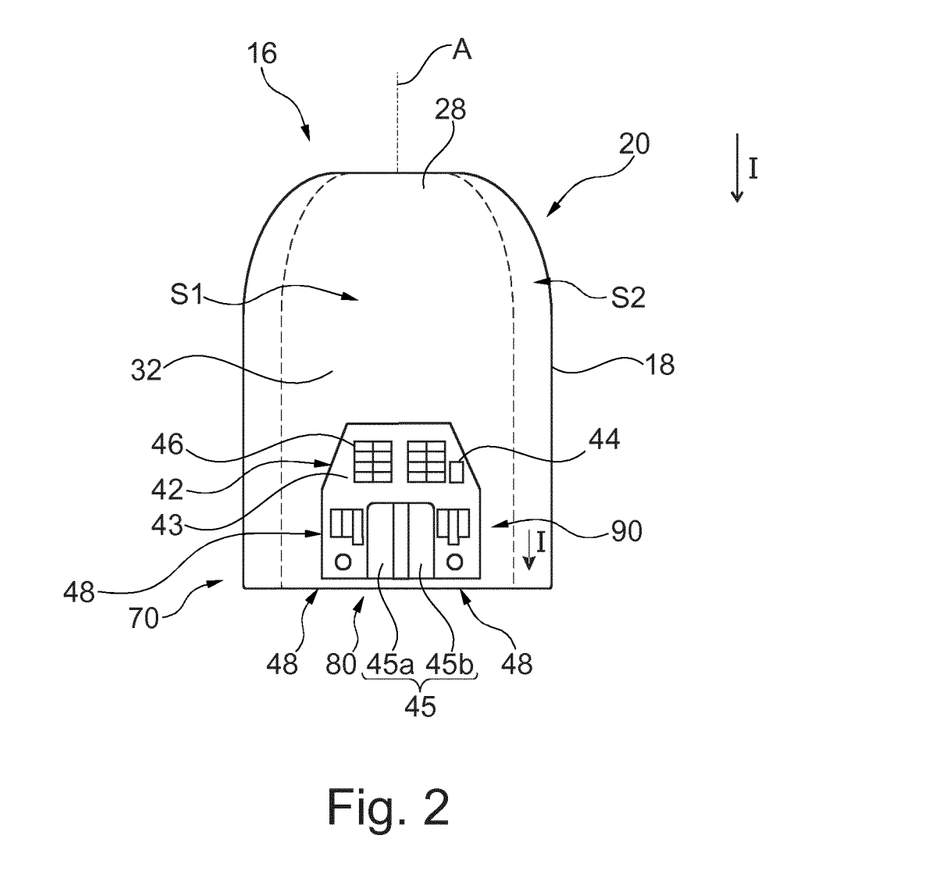
FIG. 2 is a schematic cross-sectional view of a cartridge for the electronic cigarette according to an exemplary embodiment of the present invention.

Referring to the drawings and in particular to FIGS. 1a, 1b and 2, an electronic cigarette 2 for vaporizing a liquid L is illustrated. Such an electronic cigarette 2 can be used as a substitute for a conventional cigarette. The electronic cigarette 2 has a main body 4 which may comprise a power supply unit 6, an electrical circuitry 8 and a cartridge seating 12. The cartridge seating 12 can be configured to provide a connection to a cartridge 16 comprising a vaporizing liquid L. The cartridges 16 used may be of the same or different types and be removable/disposable elements which can be replaced in order to refurbish the personal vaporizing device 2. The cartridge may also be referred to as a consumable. The electrical circuitry 8 is configured to operate the electronic cigarette 2 and may comprise a flow sensor 3 or a manual activation switch 9, a memory and a main controller 10. The electrical circuitry 8 may advantageously be grouped onto a main printed circuit board.

The cartridge seating 12 may be in the form of a recess configured to receive a cartridge 16. The cartridge and cartridge seating 12 may be provided with a cooperating fastening arrangement. The fastening arrangement may be configured as a magnetic connection means, where one of the cartridge seating 12 or the cartridge 16 is provided with a ferromagnetic member and the other is provided with a magnet. Other connection alternatives may be a snap-fit, an interference fit, a screw fit, a bayoneted fit. Additionally, or alternatively, as further illustrated in FIGS. 5a and 5b, a resilient power connector 19 can be configured as leaf spring biasing members which attaches the cartridge 16 to the cartridge seating 12 by applying a biasing force. That is to say, that the connectors or terminals of this resilient power connector means can be biased in a direction against the cartridge 16. Alternatively, or in addition, a housing 18 of the cartridge can be configured with a recess. In an embodiment, the housing 18 of the cartridge 16 and the cartridge seating 12 of the main body 4 can both be configured to snap-fit together, for instance with a recess on one of them, and a corresponding protrusion on the other one. As a more specific example, the housing 18 may have a recess on a lateral side substantially parallel to an insertion direction/of the consumable 16, i.e. the direction in which the consumable 16 is inserted to the main body 4, and this recess may correspond to a protrusion on the main body 4 for snap fitting onto the protrusion on the main body 4. In some embodiments, an insertion portion of the consumable 16 may be progressively narrower on the side which is the closest to the main body 4 when the consumable 16 and the main body 4 are connected/assembled, thus providing a guiding effect for the connection and the snap fit effect during the connection. The wording insertion refers to a connection between the main body 4 and the cartridge 16. In most of the embodiments described here-after the cartridge 16 has a portion which is inserted (i.e. enters into/penetrates) a part of the main body 4. However, the skilled person in the art easily understands that such a configuration can either be inverted with a part of the main body 4 penetrating into the cartridge 16 or with a connection which is not characterized by a penetration or the like.

As best seen in FIGS. 1b and 2, the cartridge 16 may comprise the housing 18, a liquid store 32, a vaporizing unit 34 and an electrical circuitry 42. The housing 18 may have a mouthpiece portion 20 provided with a vapor outlet 28. The mouthpiece portion 20 may have a tip-shaped form to correspond to the ergonomics of a user's mouth.

The vaporizing unit 34 may comprise a heating element 36 and a liquid transfer element 38. The liquid transfer element 38 may be configured to transfer the liquid L by capillary action from the liquid store 32 to the heating element 36. The liquid transfer element 38 can be a fibrous or porous element such as a wick made from twined cotton or silica. Alternatively, the liquid transfer element 38 can be any other suitable porous element. A vaporizing chamber 30 is defined in the area in which liquid vaporization occurs and corresponds to the proximal area in which the heating element 36 and the liquid transfer element 38 are in contact with each other.

The cartridge 16 may comprise a main channel 24 extending from the vaporization chamber 30 in the base portion of the cartridge to the vapor outlet portion 28 in the mouthpiece portion 20. The vaporizing chamber 30 is preferably located at the opposite distal end in relation to the mouthpiece portion 20. From the vaporizing chamber 30 to the vapor outlet 28 in the mouthpiece portion 20, the main channel 24 may have a uniform and tubular cross-section.

The liquid store 32 may contain a vaporizing liquid L such as propylene glycol or glycerin, which is able to produce a visible vapor. It is to be noted again that the skilled person may easily adapt the teaching of the present application to a case where the liquid is replaced by a vaporizable material (i.e. solid or viscous) known to the skilled person in that field. The personal vaporizing device 2 may be configured to produce a vapor from the liquid L to be vaporized.

The heating element 36 is not restricted to a particular type and can be a horizontal or vertical coil or a flat heating element. The cartridge 16 may be further provided with at least one air intake channel 26 extending from a first opening in the cartridge 16, through the vaporizing unit 34 and to the vapor outlet 28 in the mouthpiece portion 20. The cartridge seating 12 and or the main body 4 may also be provided with at least one air inlet opening 13.

The liquid transfer element 38 may have a tubular form and have a longitudinal direction coinciding with the longitudinal direction of the main channel 24. The tubular form provides a vapor channel 40 inside the liquid transfer element through which the vapor can leave the vaporizing chamber 30 to travel to the vapor outlet portion 28. Furthermore, the tubular form of the liquid transfer element 38 may also provide a snug fit against the inner wall of the main channel 24 and may form a space therein for receiving the heating element 36.

The heating element 36 may be a coil-shaped heater and be aligned so that its axial direction is coinciding with the longitudinal direction of the liquid transfer element 38. Hence, a coil-shaped heater can be fitted into the vapor channel 40 defined inside the liquid transfer element 38 while providing a close contact with the liquid transfer element 38. In such a way, the liquid transfer element 38 can be retained in-between the inner wall of the main channel 24 and the heating element 36. This also helps the liquid transfer element 38 to maintain its shape and avoid collapsing. The material of the liquid transfer element 38 can be cotton, silica, or any other fibrous or porous material known to the person of the art.

The cartridge 16 may be configured so that it cannot be refurbished. In other words, the liquid store 32 may be sealed or configured such that the flow circuits in the cartridge do not allow liquid to be refilled, resulting in the impossibility for a user to refurbish the liquid it contains. The advantage of a sealed liquid store 32 is that the quality and characteristic of the liquid contained will be maintained for a longer duration.

Figure 3A:
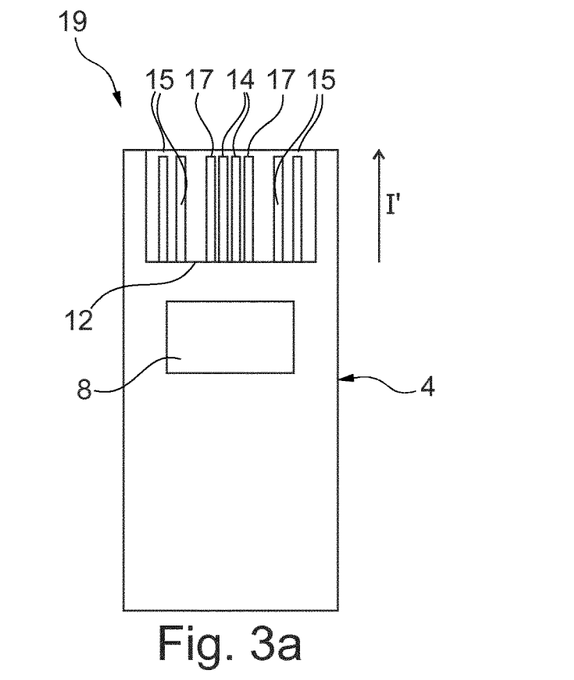
FIGS. 3a and 3b are schematic cross-sectional views of main bodies of an electronic cigarette according to two exemplary embodiments of the present invention.
Figure 3B:
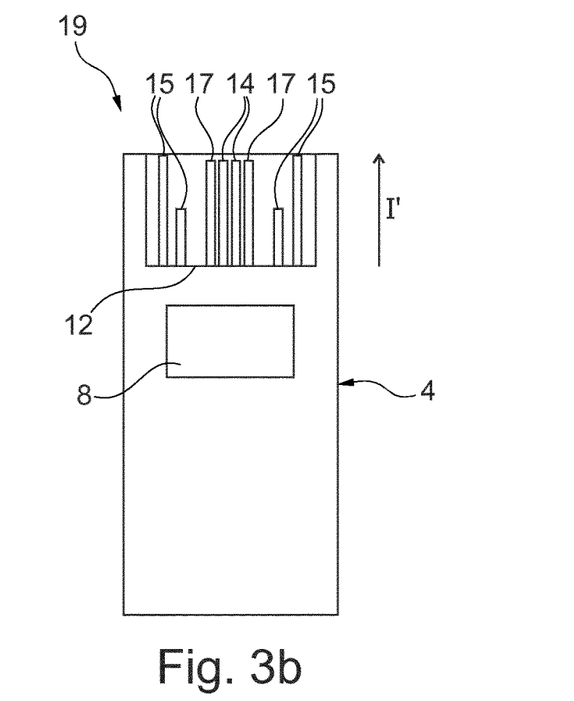

With reference to FIGS. 2 and 3, the cartridge 16 may be further provided with power terminals 45 and a cartridge electrical circuitry 42. The electrical terminals may be provided as a pair of main power terminals 45a, 45b and are connected to the heating element 36. The main power terminals 45a and 45b are thus configured to connect the heating element 36 to the power supply unit 6 via connectors 14 in the cartridge seating of the main body.

Figure 4:
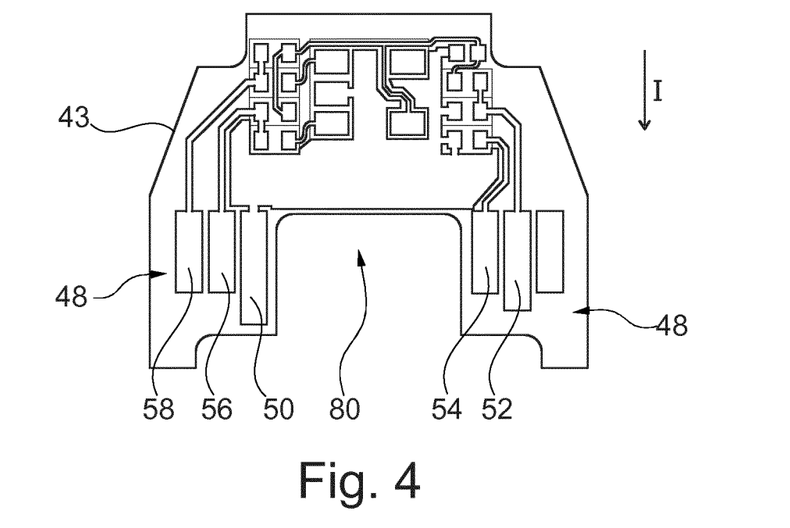
FIG. 4 is a schematic view of the electrical circuitry (PCB) of a cartridge for the electronic cigarette according to an exemplary embodiment of the present invention.

The cartridge electrical circuitry 42 may be partly or entirely placed on a PCB 43 (Printed Circuit Board) or another rigid support 43. The cartridge electrical circuitry 42 may comprise a plurality of electrical terminals 48 and a memory 44. The cartridge electrical circuitry 42 may advantageously be further provided with a controller 46, which allows for writing information onto the memory 44. The electrical terminals 48 are configured to connect the cartridge electrical circuitry 42 to the main electrical circuitry 8 of the main body 4 in order to enable the main body 4 to retrieve information from the cartridge 16. As best seen in FIG. 4, the terminals 48 may comprise data terminals 54, 56, 58 and circuit power terminals 50, 52. In a preferred embodiment, the electrical terminals 48 are provided on the printed circuit board 43, while the main power terminals 45 are provided in a cutout 80 of the PCB. Advantageously, the cutout is provided in the center of the PCB. This provides an advantage that the main power terminals 45 can be electrically isolated from the cartridge electrical circuitry 42.

Figure 5A:
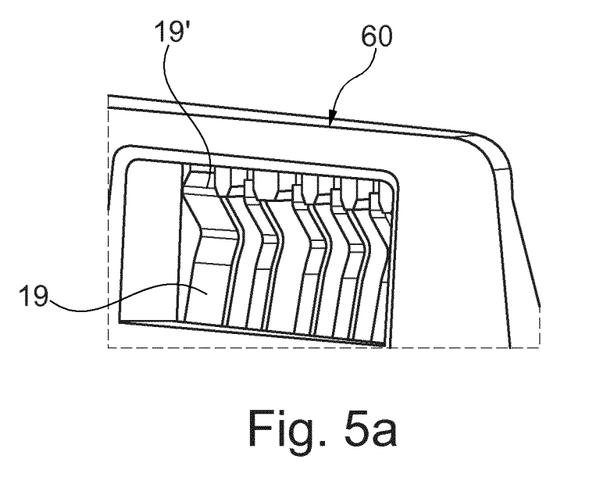
FIGS. 5a and 5b are isometric views of an electronic cigarette according to an embodiment of the present invention, where the connectors are aligned and protected by a connector guard.
Figure 5B:
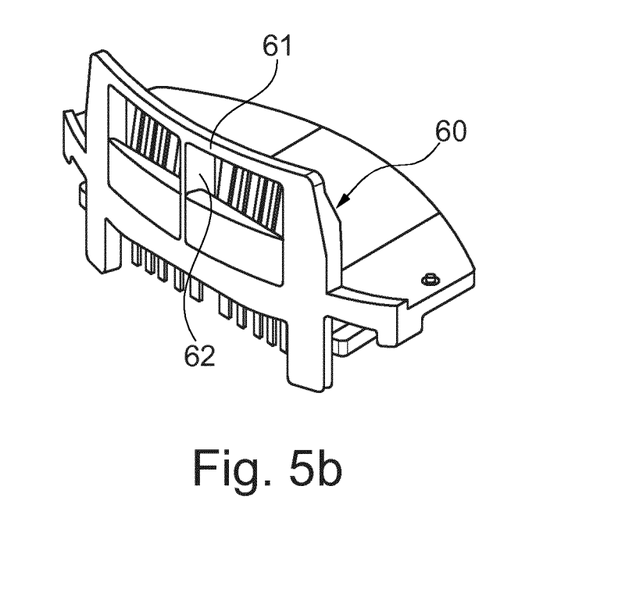

Likewise, as best seen in FIG. 3, the main body 4 of the personal vaporizing device 2 may be provided with an electrical circuitry 8, which may also be partly or entirely placed on a main PCB (not shown). The electrical circuitry 8 includes connectors 19 that are configured to establish a connection between the main electrical circuitry 8 and the cartridge electrical circuitry 42. The electrical connectors 19 comprise power connectors 14 and circuit connectors (or data connectors) 15. The power connectors 14 are configured to connect to corresponding power terminals 45 on the cartridge 16. The power connectors 14 can be configured to establish a connection between the heating element 36 and the power supply unit 6. As illustrated in FIGS. 5a and 5b, the electrical connectors 19 of the vaporizing device body 4 may be shaped as elongated contact members with a first end connected to the cartridge seating 12 and a second free end 19' configured to resiliently connect to the terminals 45, 48 on the cartridge seating 12. Hence, they can be configured as resilient "fingers". This means that the connectors 19, during connection are pressed against the terminals 45, 48, so that a force maintaining the contact between the connectors and corresponding terminals is created and the connection between them becomes more stable.

The power connectors 14 of the main body 4 may contact the first and second power terminals 45a, 45b in order to establish a power circuit providing electrical energy (current) to the heating element 36 of the consumable or cartridge 16, so as to vaporize the liquid L in the vaporizing chamber 30. This is because the heating element 36 is connected to the power terminals 45. In an advantageous embodiment, the electrical connectors 19 further comprise sensing terminals 17 configured to establish a measuring circuitry. Thus, the second pair of electrical connectors 17 may measure a voltage between the first and the second power terminals 45, and this voltage may be used for determining precisely the temperature of the heating element 36, for instance through the determination of the resistance of this heating element 36. This feature will be described later in more detail.

As is shown in FIGS. 5a and 5b, the free ends 19' of the electrical connectors 19 may be retained in a connector guard 60. The connector guard 60 may protect the free ends 19' of the electrical connectors 19, from being physically damaged as a result of a wrongly performed connections between the main body 4 and the cartridge 16 or due to the accidental introduction of a foreign object. In particular, the connector guard 60 may protect the extremities/endpoints of the free ends 19' of the electrical connectors 19, or at least one side of the arrangement of electrical connectors 19, or the backside of the electrical connectors (i.e. the other side of the connector, which is not in contact with the electrical terminals 45, 48). This protection ensures that the extremities of the connectors 19' are not wrongly touched or contacted and consequently, damaged in any way such as being deformed by foreign objects getting into the cartridge seating 12 or by a cartridge 16 being wrongly inserted into the main body. Even more advantageously, the connector guard 60 may protect a combination of the sides mentioned above, or all of them. In more details, the connector guard 60 may be provided in a T-form, with a supporting bar 62 protruding from the cartridge seating 12 and with a top protective extension 61 being substantially parallel to an alignment direction of the arrangement of electrical connectors to be protected. The connector guard 60 may also be provided in an inverted U-form or substantially in an m-form, placed around the electrical connectors 19. The connector guard 60 may also be provided in the form of a cage open on the connection side (i.e. the side of the surface of the electrical connectors which contacts the electrical terminals 45, 48) and closed on the backside. The connector guard 60 may also have a base portion, which covers and maintains the ends of electrical connectors, which are connected to the cartridge seating 12. This base portion is advantageously provided in the form of a bar substantially parallel to the alignment direction of the arrangement of electrical connectors being aligned by the connector guard 60.

Referring back to FIG. 2, the data stored in the memory 44 of the cartridge 16 can comprise one or several sets of usage data of the cartridge 16. The data may include authentication data of the cartridge 16, data identifying the type, composition, flavor or remaining quantity of a liquid L contained in the cartridge 16, and/or best-before date of consumption of the cartridge 16. The electrical circuitry 8 of the main body 4 may be configured to retrieve and process this data, for instance to control the operating mode of the heating element 36 in accordance with the data. As an example, it may regulate the power which is applied to the heating element 36 in the cartridge 16 through the power circuit depending on the temperature or the resistance of the heating element 36 determined as explained above. The main controller 10 can be configured to read and write data on the cartridge memory 44, for instance the main controller 10 can estimate the consumed amount of liquid from a specific cartridge and write the information on the cartridge memory 44. This advantageously enables the user to keep track of consumed amounts of liquids from different cartridges 16 even if the cartridges are being used in an alternating manner.

As shown in FIG. 1b, the main body 4 of the electronic cigarette 2 may further comprise a communication unit 11. The communication unit 11 may be configured to transfer the data retrieved and processed by the main body 4 to other systems, devices or networks, for instance via Bluetooth to an Internet-enabled device such as a smartphone, with the possibility to further transfer this data to a server for reporting or further analysis (e.g. to receive a recommendation to order more cartridges).

FIGS. 2 and 3 also illustrate advantageous arrangements for the electric connection between a cartridge 16 and a main body 4 of an electronic cigarette 2. As illustrated in FIG. 2, a cartridge 16 may comprise a connection portion 70 arranged as a distal portion of the cartridge 16 which is opposite to the mouthpiece portion 20. This connection portion 70 may have one lateral surface 90 (in the case it has a cylindrical or substantially cylindrical form) or several lateral surfaces 90, in case the connection portion 70 has a for instance rectangular cross section. The one or more lateral surfaces 90 may be a plane in a direction coinciding with the axial direction A of the cartridge 16 (going from the connection portion 70 to the mouthpiece portion 20). The one or more lateral surfaces 90 may be flat or curved. It is advantageous with a flat connection portion as for manufacturing efficiencies it is easier to produce flat circuit boards. The circuit terminals 48 may be located in said connection portion 70 on the lateral surface 90, advantageously in the furthest part of the lateral surface 90 from the mouthpiece portion 20. In some embodiments, the cartridge 16 has a first S1 and a second pair of lateral sides S2 substantially parallel to each other, the widths of the sides of the first pair S1 being wider than the widths of the sides of the second pair S2, and said lateral side on which the circuit terminals 48 are located is one of the sides of the first pair S1. Such configurations provide more stability and open more possibilities in terms of distributing the various connectors or terminals over their respective arrangement surface.

As seen in FIGS. 2 and 4, the circuit terminals 48 can be arranged at different longitudinal positions in relation to the longitudinal direction (axial direction A) of the cartridge 16. In an embodiment, the circuit terminals 48 can be elongated with their longitudinal direction substantially parallel to an insertion direction I of the consumable 16. Advantageously, the circuit terminals 48 are arranged on the same plane. Such configurations provide a more stable electrical connection between the consumable 16 and the main body 4. In some embodiments, the distance between two neighboring circuit terminals 48 may be comprised between 20 mm and 0.05 mm, preferably 10 mm and 0.1 mm, more preferably 5 mm and 0.15 mm, even more preferably 1 mm and 0.05 mm. Such distance ensures a compact distribution of the plurality of terminals 48 whilst maintaining enough distance between them, so that when the main body 4 and the cartridge 16 are connected/assembled, the circuit terminals 48 are connected to their corresponding connectors 19, with less risk of a connection between non-corresponding pairs of connectors/terminals.

As the circuit terminals 48 of the cartridge 16 can be arranged at different longitudinal positions in relation to the longitudinal direction of the cartridge 16, the circuit terminals 48 are configured to be connected sequentially (i.e. at different times) to their corresponding circuit connectors 19. In particular this is easily achieved if the corresponding circuit connectors are all aligned as illustrated in FIG. 3a. It should be noted that such a configuration can also be achieved as illustrated in FIG. 3b, in the case that the circuit terminals 48 of the cartridge 16 are all aligned at the same longitudinal position but one or more connectors 19 of the main body extend to a different extent in the connecting direction I' of the main body 4, i.e. the direction in which the main body 4 is connected to the consumable 16. Alternatively, the combination of the position of the terminals 48 on the cartridge 16 and the length of the connectors 19 in the cartridge seating 12 can both be un-aligned as long as they enter in contact with their respective counterparts at different times when the cartridge 16 is inserted. It is clear that both the position of the terminals 48 and the length of the connectors 19 determine the sequence in which data terminals 48 and connectors 15 are connected. In other words, the circuit terminals 48 of the cartridge 16 and the connectors 19 of the main body may be configured such that one or more of the circuit terminals 48 are connected to the corresponding circuit connectors 19 at different times when the consumable 16 is connected to the main body 4.

The cartridge 16 therefore has circuit terminals 48, or at least initial connection portions thereof, provided at different positions in the longitudinal direction of the cartridge relative to the longitudinal positions of the circuit connectors 15, or at least initial connection portions thereof, whereby the circuit terminals are connectable to the circuit connectors in a predetermined sequence upon connection of the cartridge to the main body of the electronic cigarette. Note that the initial connection portions of the circuit terminals or the circuit connectors are the end portions of those terminals or connectors, which first encounter their corresponding connector or terminal when the cartridge is inserted into the cartridge seat of the main body in the normal insertion manner by a user. Clearly, the sequence of connection can be controlled by varying the length or position of the terminals and/or connectors in the longitudinal direction such that the initial connection portions of corresponding terminal/connector pairs encounter each other at different timings upon normal insertion of the cartridge into the cartridge seat in which the cartridge is received by the main body.

Although, as mentioned above, the sequencing may be controlled by controlling the longitudinal positions of the initial connection portions of the terminals and/or the connectors, it is advantageous if the longitudinal positions of the connectors 48 of the cartridge are varied since this enables different sequencing to be obtained for different cartridges—e.g. in order to take into account the actual electronics contained on the cartridge (e.g. because a new version of a cartridge has been produced using different electronics to the original version which will better suit a different sequence of connection compared to the original cartridge) without requiring a change to the main body of the device (so that the "old" device can still be compatible with the new cartridge).

It should be noted that such sequential configuration can be extended to any of the electrical connectors 14, the sensing terminals 17, the data connectors 15, so that a specific sequence of connection of all the connectors with their respective terminals 45, 48 can be achieved. An example will be provided later in the description.

Figure 6:
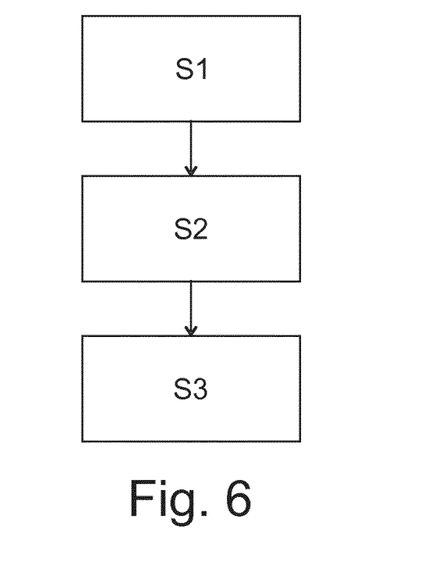
FIG. 6 is a schematic of a method for connecting sequentially the terminals and connectors of the electronic cigarette according to an exemplary embodiment.

As best seen in FIGS. 4, the circuit terminals 48 on the cartridge 16 may comprise a negative circuit terminal 50, a cartridge sensing terminal 54, a data transfer terminal 56 and a timing circuit terminal (SCL) 58 configured to synchronize data and determine which data is valid to be recorded and a positive power terminal 52 arranged to supply power to the other terminals 50, 54, 56 and 58. In a preferred embodiment (see FIG. 6), the negative circuit terminal 50 is connected in a first step S1. By connecting the negative circuit terminal 50 first, the negative circuit terminal 50 will act as ground and is able to divert electric charges in the cartridge circuitry 42 back to the power supply unit 3. In order to provide power to the electrical circuitry 42, the positive power terminal 52 is connected in a second step S2. In a third step S3, the remaining terminals can be connected simultaneously or sequentially.

The cartridge-sensing terminal 54 is configured to enable the main controller to determine if a cartridge is connected to the seating. A resistor is included in this circuit and between the terminals in the device, the device circuitry is therefore configured to read a voltage drop when a cartridge 16 is present in the cartridge seating 12. The connectors 19 in the cartridge seating 12 are configured to establish a measuring circuit including the cartridge sensing terminal 54 and the main controller 10 in order to detect a voltage and determine by the controller that a cartridge 16 is present in the cartridge seating 12. The resistor in the cartridge can be a pull-down resistor (or even a direct connection) connected between the cartridge sensing terminal 54 and the negative circuit terminal 50 (or any portion connected thereto acting as ground) in the cartridge. The resistor in the vaporizing device can include a pull-up resistor (connected between the connector 19, which connects to the cartridge sensing terminal 54, and a voltage Vcc) having a greater resistance than the pull-down resistor in the cartridge. Thus, when a cartridge is inserted into the main body, the voltage at connector 19 falls from a high voltage (controlled by the pull-up resistor) to a low voltage (controlled by the pull-down resistor in the cartridge) and thus drop in voltage at the connector 19 is detected by the main controller.

Also, the power terminals 45 of the cartridge 16 may be elongated and arranged with their longitudinal direction substantially parallel to the insertion direction I of the consumable 16. Furthermore, all the power terminals 45 may be arranged on the same plane. These configurations provide the same advantages as similar configurations of the other terminals. Furthermore, the power terminals 45 may be located on the plane of the circuit terminals 48, improving the overall electrical connection between the cartridge 16 and the main body 4. In some embodiments, the distance between two neighboring power terminals 45 may be comprised between 30 mm and 0.05 mm, preferably 10 mm and 0.1 mm, more preferably 5 mm and 0.15 mm, even more preferably 2 mm and 0.2 mm, even most preferably 1 mm and 0.2 mm. The power terminals 45 have a width of between 1.0 mm and 3.5 mm, preferably between 1.5 mm and 2.5 mm, and most preferably between 2.0 mm and 2.5 mm.

According to another advantageous aspect of the invention, the power terminals 45 may extend further in said insertion direction I of the cartridge 16 than the circuit terminals 48, allowing a power connection (i.e. a connection of the power terminals 45 with the electrical connectors 14 and/or 17) to take place before the data connections (i.e. the connections between the circuit terminals 48 and the circuit connectors 19) is established. In other words, the electronic cigarette 2 may be configured such that the power terminals 45 are connected to the power connectors 14 before the circuit terminals 48 are connected to the circuit connectors 19 when the cartridge 16 is inserted into the main body 4. As a result, there is a delay between the moment in which the electrical circuitry 42 of the consumable 16 is turned on/receives power and the moment in which the data connection is established. It should be noted that such a configuration can also be achieved in the case that the ends of the power terminals 45 are aligned with the ends of the circuit terminals 48 but the power connectors 15 of the main body protrude further in the connecting direction 51 of the main body 4 than the connectors 19.

According to a yet further advantageous aspect of the present invention, the cartridge sensing terminal 54 may extend further in said insertion direction I of the cartridge 16 than the data transfer terminal 56 and the timing circuit terminal (SCL) 58, allowing the sensing terminal 54 to be contacted and a sensing circuit to be established before the controller 10 starts the interrogation of the cartridge memory 44. This improves the reliability of the data connection (by avoiding a current surge associated with the connection of the cartridge sensing terminal 54 from interfering with a data transmission) and thus speeds up the authentication process of the cartridge 16.

It is to be noted that in general, the configurations presented above in the various embodiments are easily invertible: that is to say that the skilled person can easily bring some configurations/elements of the connection between the main body 4 and the cartridge 16 in the other piece of the electronic cigarette 2. For instance, the skilled person can easily and obviously transfer the teaching of the present application to a case where the main body 4 is inserted into the cartridge 16, and the cartridge 16 is provided with a main body seating where its terminals are aligned and protected by a terminal guard.

The second pair of electrical connectors 17 may contact the first and second power terminals 45a, 45b in order to establish a measuring circuitry for determining the temperature of the heating element 36. Thus, the second pair of electrical connectors 17 are configured to measure a voltage between the first and the second power terminals 45a, 45b. In other words, the power circuit may be a current carrying circuit for powering the heating element 36 with energy from the main body 4, and the measuring circuit may be a voltage sensing circuit. Such a measuring configuration, which is sometimes referred to as "four terminal sensing" or "Kelvin sensing", allows a determination of the impedance/resistance of the heating element 36 or, more precisely, of the circuit between the two power connectors 45 including the heating element 36 from the measured voltage. The advantage of the use of these two separate circuits is that the measurement of the impedance/resistance of the heating element 36 (or of the circuit which contains the heating element 36), and consequently the determination of the temperature of the heating element 36, is more accurate than in the situation where only one circuit is used. This is because the separate measuring circuit enables measurement of resistance over the heating element 36 while excluding the resistance of the wires and welds from the measurement. The main body 4 may be provided with a controller 10 configured to receive information of the measured voltage from the voltage sensor and determine the operating temperature of the heating element 36.

The memory 44 of the consumable 16 may be storing or be configured to store a first reference value indicating the resistance of the heating element 36 at a reference temperature or reference temperature range of the heating element 36, for example at room temperature. The reference value enables the determination of the relationship between a measured resistance and a temperature.

The reference resistance value can advantageously be determined in the manufacturing process and then programmed into the cartridge memory 44. This will be later described in more detail.

The controller 10 of the main body 4 is configured to obtain the reference value from the cartridge memory 44. Hence, the controller 10 of the main body 4 is configured to obtain the first reference value indicating the resistance of the heating element 36 at a reference temperature or reference temperature range of the heating element 36, and to determine the temperature of the heating element 36 by means of comparing the determined resistance with the resistance indicated by first the reference value.

The main controller 10 of the personal vaporizing device 2 may be further configured to regulate the power (e.g. pulse-width modulation), which is applied to the heating element 36 in the consumable 16 through the power circuit depending on the determined temperature. This provides a temperature regulation of the vaporizer to ensure that the temperature is optimal in respect to the vapor generation but also to avoid undesired components being formed and a dry wick situation where the heating element 36 is generating heat even though the liquid store 32 or the liquid transfer element 38 are empty or dry. It is to be noted that the determination of the temperature can also be made implicitly in the technical implementation of the present invention. More precisely, since the present invention lies partly on the concept of determining a temperature through a resistance value of the heating element 36, whose resistance varies with the temperature, it is easily understandable to the skilled person that the regulation of the power to be applied to the heating element 36 can also be made just by determining the resistance and matching the resistance value with the power to be applied, provided that at some point of the technical implementation, a matching between the temperature of the heating element 36 and its resistance has been made.

Thus, a method for determining the temperature of the heating element 36 in a consumable 16 of an electronic cigarette 2 as described above comprises the determination of the actual resistance of the circuit in the consumable 16 including the heating element 36 between the first 45a and second 45b power terminals. Any known method for determining the resistance can be used, but the preferred method comprises a step of measuring a voltage over the pair of power terminals 45a, 45b, and such a step can be performed by the controller 10 of the main body 4. In more detail, the first and second power terminals 45a, 45b of the consumable 16 can be contacted by the first pair of electrical connectors 14, so that a measuring circuit is established and the controller of the main body 4 can measure the voltage between the first and second power terminals 45a, 45b. The actual resistance of the circuit in the consumable 16 including the heating element 36 between the first and second 45 power terminals is determined by means of the measured voltage, in the way as is known to the skilled person. During use, only the temperature and thus the resistance of the heating element 36 will substantially increase. Hence, the present method provides an accurate temperature measurement even though negligible changes in temperature will occur in the remaining parts; this is also possible as the other parts are made of materials, which demonstrate a smaller temperature coefficient of resistivity. Therefore, the actual temperature of the heating element 36 can be determined or estimated based on the measured resistance of the open loop.

Figure 7:
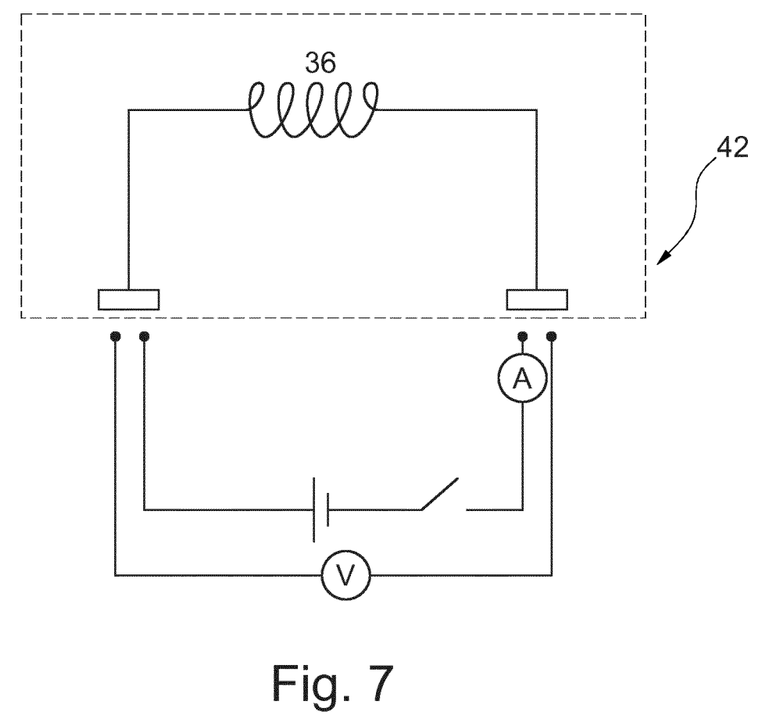
FIG. 7 is a schematic of an open loop.

Optionally, as shown in FIG. 7, the main controller 10 may also be configured to obtain, in addition to the first reference value, a second reference value which allows to determine the difference between the resistance of the heating element 36 and an open loop of an electronic circuit 42 including the heating element 36. In this case the controller 10 is configured to determine the value of the actual resistance of the heating element 36 by subtracting the difference between the resistance of the heating element 36 and the open loop of an electronic circuit 42 including the heating element 36.

The determination is even more accurate if a reference value (herein referred to as "second" reference value) is obtained which allows to determine the difference between the resistance of the heating element 36 and that loop at a reference temperature or reference temperature range. The memory 44 of the consumable 16 may be further configured to store this second reference value which allows to determine the difference between the resistance of the heating element and an open loop of an electronic circuit 42 including the heating element 36. For example, if the second reference value indicates the resistance of the entire loop between the first 45a and second 45b power terminals at room temperature, the actual resistance of the heating element 36 is: actual resistance value of the loop between the first 45a and second 45b power terminals−second reference value+first reference value, wherein the "first" reference value indicates the resistance of the heating element 36 at room temperature. If the second reference value indicates the difference between the resistance of the entire loop heating and the element 36 alone, at room temperature, the current resistance of the heating element 36 is: current resistance value of the loop between the first 45a and second 45b power terminals−second reference value.

The above-mentioned first and second reference values can be stored in and obtained from a memory of the main body. However, in the preferred embodiments, the reference values are obtained from the memory 44 of the cartridge 16 because the reference values will typically be different for different cartridges 16. For instance, the controller 10 may access the memory 44 by means of the data circuit established by the connection of the data terminals 48 and the data connectors 19, as described above. Alternatively, an estimation of the second reference value can be obtained by the electronic cigarette by measuring the current resistance of the loop in the cartridge 16 including the heating element 36 between the first 45a and second 45b power terminals at an ambient temperature prior to commencing heating of the heating coil; however, such an approach is subject to significant inaccuracies unless the ambient temperature can be controlled to be very close to the reference temperature. Accordingly, it is preferred if the second reference value is determined at manufacture in the manner explained below after explaining how preferably to determine the first reference value.

Once the actual resistance of the heating element 36 has been determined, either by use of a second reference value or not, the actual temperature of the heating element 36 can then be determined by means of comparing the determined current resistance with the resistance indicated by the first reference value. The cartridge memory 44 may therefore further comprise the interrelationship between resistance values and temperatures. Additionally, the cartridge memory 44 may further comprise a program to control the power supply or the pulse-width modulation in response to the determined actual temperature. Such method makes use of the concept of matching a resistance of the heating element 36 to its temperature by means of the resistance characteristics of the heating element, which can be derived from the first reference value indicating the resistance of the heating element 36 at a reference temperature or temperature range, e.g. at room temperature, together with knowledge of the temperature coefficient of resistivity of the heating element.

It is preferable if the heating element 36 is made from a material which has a substantially constant coefficient of resistivity with temperature, but if it doesn't it will be apparent to a person skilled in the art how to adapt the equations used—e.g. substituting the single equation with a series of equations using different approximations to the coefficient of resistivity at different temperatures (i.e. approximating the real situation to a series of linear equations over a series of temperature ranges between ambient temperature and the operating temperature of the heater—e.g. approximately 250° C., etc.). That is to say—for instance—that, knowing that the resistance values for conductors at any temperature other than the standard temperature (usually specified at 20° C.) can be determined through the following formula:

$$R = R\text{ref}[1 + \alpha(T - T\text{ref})]$$

Where R is the current resistance of the coil at the current temperature T, Rref is the reference resistance of the coil at reference temperature (usually 20° C.), α is the temperature coefficient of resistance of the coil material, T is the coil current temperature in ° C. and Tref is the reference temperature. The temperature of the coil can be obtained by the following equation:

$$T = T\text{ref} + (1/\alpha)([R/R\text{ref}] - 1).$$

Such a formula can also be saved in the form of a function T=f(R), a graph or a relationship table.

Alternatively, a table specifying the inter-relationship between the temperature at the heater versus the measured resistance of the heater could be stored in a memory in the main body 4. To account for different cartridges having heaters with variations in inherent resistance, some parameters may be stored on the cartridge memory in addition to the reference values. Parameters stored on the cartridge memory may include properties of different heater types (e.g. made of different materials having different temperature dependent coefficients of resistivity) directly or identifiers of different predetermined heater types, enabling the main controller to access a correct corresponding table stored on the main body specifying the relationship between coefficient of resistivity and temperature, etc.

In an advantageous embodiment, the material of the heating element 36 can be titanium. Titanium has a steep resistance to temperature curve in comparison with e.g. stainless steel or nickel. Hence, the resistance of the heating element 36 increases relatively rapidly with an increasing coil temperature. However, other materials such as Stainless steel, Nickel, Chrome or Aluminium or alloys thereof are also possible. The heating element 36 design and its geometry also influence the resistance of the heater by the length and diameter of the heating element. The geometry of the heating element 36 is selected to match the dimension and characteristics of the liquid transfer element 38 and such that a desired vaporization operation can be achieved. For the present method of establishing a temperature and resistance relationship it is advantageous that the selected material demonstrates a replicable functional relationship between resistance and temperature. Depending on the desired accuracy of the temperature measurement, different ways of estimating the temperature coefficient of resistance a of the heating element material can be implemented.

In an advantageous embodiment, the temperature coefficient of resistance a of the heating element material can be assumed as being constant. This is because it has been found that in the interval of between about 20° C. and about 250° C. the resistance increases linearly with an increasing temperature. In theory, during the manufacturing process the heating element resistance could simply be measured at the reference temperature of the heating element (e.g. by controlling the ambient temperature to be at the reference temperature). However, it is advantageous to measure the heating element 36 at the ambient temperature in the manufacturing facility (without controlling the ambient temperature to be exactly the same as the reference temperature). The ambient temperature can be different from 20° C., such as 25° C. In an example where the ambient temperature is 25° C., the resistance of the heating element at 20° C. in an example is calculated to be around 0.270Ω by using the formula as per above and the α of 0.00413 per degree Celsius. The resistance of the heating element 36 at 250° C. is then calculated for this example using the same value for α of 0.00413 per degree Celsius and found to be around be 0.526Ω. The electrical resistivity for the present heating element 36 in titanium in this example has been identified as 456 nΩ·m (at 20° C.) and 888 nΩ·m (at 250° C.).

In an exemplary method, each heating element 36 is measured before being assembled into the cartridge 16. The heating element 36 and the PCBA are preferably mounted onto a fixture so that they can be held firmly in place. The PCBA and the heating element 36 are connected to a test computer and measurement circuit comprising a program that enables measuring, collecting data and writing data on the memory of PCBA (e.g. EEPROM).

An exemplary measurement method can be as follows: In a first step, the heating element 36 resistance is measured. In a second step, the ambient temperature is measured. In a third step, the controller determines if the ambient temperature is different from 20° C. In an optional fourth step, the heating element 36 resistance at 20° C. is calculated if the ambient temperature is different from 20° C. This resistance is calculated by the formula R=Rref[1+a(T−Tref)] and with the value of a determined by the inherent material characteristics. For example, where the heating element 36 is made from titanium a value for α of 0.00413 per degree Celsius can be used. In a fifth step, the coil resistance is written into the EEPROM at 20° C. The test computer can be used to write the information on the PCBA. In a sixth step, heating element resistance is read out from the EEPROM and is verified. The heating element 36 and PCBA are thereafter removed from the fixture. Optionally, the log file is filed into the local disk. This enables measurements from different heating elements to be stored. The test configuration is reset such that a new heating element can be set up in the fixture.

Optionally, the EEPROM can be programmed with other types of information while it is mounted in the fixture. For instance, the EEPROM can be programmed with a serial number, information about the liquid type and quantity in the cartridge 16, manufacturing date and expiration date etc.

The present invention also relates to a method of regulating the power applied to a heating element 36 in a consumable 16 of a personal vaporizing device 2. For doing so, a feedback loop is executed, comprising: determining the temperature of the heating element 36 in accordance with one of the above-described methods for determining this temperature, and regulating the power supplied to the heating element 36 depending on the determined temperature. The skilled person will understand that it is not necessary to explicitly determine the temperature of the heating element 36. Rather, the value of the current resistance of the heating element determined in accordance with the above-mentioned method can be directly translated into a value for the power to be applied to the heating element 36, e.g. by means of a translation table or formula. Thus, as used herein, the expression "determining the temperature of the heating element by means of comparing the current resistance of the heating element with the resistance indicated by a reference value" also encompasses an implicit determination of the temperature, where a value like a control value is determined directly from the current resistance of the heating element 36 by using a table, formula or the like which has been established on the basis of the relationship between the resistance and the temperature of the heating element 36.

The method of manufacturing a cartridge 16 according to the present invention may comprise a step of obtaining the first reference value by measuring the resistance of the heating element 36, preferably before its assembly into the consumable 16, while the temperature of the heating element 36 substantially corresponds to the reference temperature or lies within the reference temperature range. Preferably, however, the method of manufacturing a cartridge 16 according to the present invention may comprise obtaining a first reference value by: measuring the resistance of the heating element 36, prior to is assembly into the cartridge 16; measuring the temperature of the heating element 36 (e.g. by measuring the ambient temperature of the environment of the heating element and ensuring that the heating element will be approximately at the ambient temperature of the environment—e.g. by ensuring that the heating element has had sufficient time to heat up or cool down to the ambient temperature and has not recently been subjected to heating or cooling manipulations or processes etc.); and then by determining the expected resistance of the heating element at a predetermined reference temperature (e.g. 20° C.) and storing this determined expected resistance as the first reference value. Preferably, the determination of the expected resistance value is calculated using knowledge of the temperature coefficient of resistivity of the material used to make the heating element at a predetermined reference temperature, e.g. by using the following formula (or it's equivalent): Rref1=Rmeasured(1−α(Tmeasured−Tref)) where Rref1 is the first reference value, Rmeasured is the resistance of the heating element as measured, α is the coefficient of resistivity of the material of which the heating element is made at the reference temperature, Tmeasured is the measured temperature of the heating element and Tref is the reference temperature (e.g. 20° C.). The first reference value determined in this way can be stored in the memory 44 of the cartridge so that it can be accessible to the controller 10 of the main body 4 during the use of the personal vaporizing device 2. The resistance value provided by the manufacturer of the heating element is usually subject to production tolerances. By storing the exact value measured on the specific heating element 36 mounted onto the cartridge 16, the controller 10 of the main body 4 can use a more accurate value for its determination of the temperature of the heating element 36 based on the measured current resistance value.

Where the cartridge is also to store the second reference value, which allows to determine the difference between the resistance of the heating element 36 and the loop in the cartridge 16 including the heating element 36 between the first 45a and second 45b power terminals at a reference temperature or reference temperature range, this second reference value can be obtained during manufacture by measuring the resistance of the open loop (preferably also using a four wire measurement technique) after the assembly of the open loop while the temperature of the heating element 36 substantially corresponds to a measured temperature (e.g. a measured ambient temperature of the manufacturing environment) and calculating the expected resistance of the open loop at the reference temperature based on the measured resistance of the open loop at the measured temperature (e.g. by accounting for the difference in resistance of the heating element at the reference temperature compared to the expected resistance of the heating element at the measured temperature. The thus obtained expected resistance of the open loop at the reference temperature or a value derived therefrom (such as the difference between the expected resistance of the open loop at the reference temperature and the first reference value, to thereby obtain an estimate of the combined resistance of the components contained in the open loop (e.g. wires, terminals, conductive tracks, etc.) other than the heating element, can also preferably be stored in the memory 44 of the cartridge, just like the first reference value.

The invention claimed is:

1. A cartridge for a personal vaporizing device, the cartridge comprising:
   a liquid store,
   a liquid transfer element,
   a heating element,
   a first power terminal and a second power terminal connected to the heating element, and
   a memory storing a first reference value indicating resistance of the heating element at a reference temperature or a reference temperature range of the heating element,
   wherein the memory stores a second reference value indicating resistance of an open loop of an electronic circuit, the open loop extending between the first and second power terminals and including the heating element.

2. The cartridge according to claim 1, wherein the memory further comprises a predetermined temperature coefficient of resistivity related to a material of the heating element.

3. The cartridge according to claim 1, wherein endpoints of the open loop are the first and second power terminals.

4. The cartridge according to claim 1, further comprising one or more data terminals configured to provide the first and/or second reference values to a main body of the personal vaporizing device.

5. The cartridge according to claim 1, wherein the cartridge further comprises a mouthpiece portion.

6. A method of manufacturing the cartridge according to claim 1, wherein the first reference value is obtained by measuring the resistance of the heating element and measuring an ambient temperature.

7. The method according to claim 6, wherein the ambient temperature substantially corresponds to a temperature of the heating element and/or to the reference temperature.

8. The method according to claim 6, wherein the ambient temperature corresponds to a temperature of the heating element, which differs from the reference temperature, and wherein a resistance reference value at the reference temperature is calculated by adjusting the measured resistance of the heating element by using the formula $R=R_{ref}[1+\alpha(T-T_{ref})]$, where R is a current resistance of the heating element at the ambient temperature, $R_{ref}$ is the reference resistance value of the heating element at the reference temperature $T_{ref}$, $\alpha$ is a temperature coefficient of resistance of a material of the heating element and T is a current temperature in ° C. of the heating element.

9. A method of manufacturing the cartridge according to claim 1, wherein the first reference value is obtained by measuring the resistance of the heating element and measuring an ambient temperature, wherein the ambient temperature substantially corresponds to a temperature of the heating element and/or to the reference temperature, and wherein obtaining the second reference value includes a step of measuring the resistance of the open loop after assembly of the open loop while a temperature of the heating element substantially corresponds to the reference temperature or lies within the reference temperature range.

10. A method of manufacturing the cartridge according to claim 1, wherein the first reference value is obtained by measuring the resistance of the heating element and measuring an ambient temperature before assembly of the heating element into the cartridge.

11. A main body of a personal vaporizing device, the main body having a cartridge seating configured to receive a cartridge comprising:
    a heating element,
    a first power terminal and a second power terminal connected to the heating element to thereby form an open loop between the first and second power terminals, which form endpoints of the open loop, and including the heating element connected between the first and second power terminals; wherein the cartridge seating comprises:
    a first pair of electrical connectors configured to establish an electrical circuit when connected to respective ones of the first and second power terminals of the cartridge whereby power may be supplied to the heating element from the main body via the first pair of electrical connectors and the first and second power terminals, and
    a second pair of electrical connectors configured to establish a measuring circuit when connected to respective ones of the first and second power terminals for measuring voltage between the first and second power terminals of the cartridge whilst power is supplied to the first and second power terminals via the first pair of electrical connectors.

12. The main body according to claim 11, wherein the main body further comprises a controller configured to determine resistance of the open loop between the first and second power terminals by the voltage measured by the measuring circuit; and
    to determine an estimate of resistance of the heating element on the basis of the determined resistance of the open loop.

13. The main body according to claim 12, wherein the controller is further configured to obtain a first reference value indicating the resistance of the heating element at a reference temperature or a reference temperature range of the heating element; and to determine an estimate of a temperature of the heating element by comparing the determined resistance of the open loop with the resistance indicated by the first reference value.

14. The main body according to claim 13, wherein the controller is further configured:
- to determine a difference between the resistance of the heating element and the resistance of the open loop based on the obtained second reference value; and
- to determine an estimate of a value of the current resistance of the heating element by subtracting the determined difference between the resistance of the heating element and the resistance of the open loop from the determined resistance of the open loop.

15. The main body according to claim 14, wherein the controller obtains the first and/or second reference values from the cartridge.

16. The main body according to claim 15, further comprising data connectors for obtaining the first and/or second reference values from the cartridge.

17. The main body according to claim 12, wherein the controller is configured to determine a current temperature by executing a functional relationship of $R = R_{ref}[1+\alpha(T-T_{ref})]$,
where R is a current resistance of the heating element at an ambient temperature T, $R_{ref}$ is a reference resistance value of the heating element at a reference temperature $T_{ref}$, $\alpha$ is a temperature coefficient of resistance of a material of the heating element and T is a current temperature in ° C. of the heating element.

18. The main body according to claim 17, wherein the main body is configured to regulate power applied to the heating element in the cartridge depending on the determined current resistance or current temperature of the heating element.

* * * * *